United States Patent [19]

Leinen et al.

[11] Patent Number: 5,294,640
[45] Date of Patent: Mar. 15, 1994

US005294640A

[54] FUNGICIDAL SOLUTION

[75] Inventors: Hans Theo Leinen; Gerhard Schachtlbauer, both of Duesseldorf; Wolfgang Gress, Wuppertal-Elberfeld, all of Fed. Rep. of Germany

[73] Assignee: Henkel Kommanditgesellschaft auf Aktien, Duesseldorf, Fed. Rep. of Germany

[21] Appl. No.: 64,180

[22] Filed: May 25, 1993

[30] Foreign Application Priority Data

Nov. 26, 1990 [DE] Fed. Rep. of Germany ....... 4037504

[51] Int. Cl.$^5$ ...................... A01N 37/34; A01N 43/50
[52] U.S. Cl. ...................... 514/525; 514/392
[58] Field of Search ................. 514/392, 525

[56] References Cited

U.S. PATENT DOCUMENTS

| | | | |
|---|---|---|---|
| 3,816,505 | 6/1974 | Watts, Jr. | 260/454 |
| 3,948,636 | 4/1976 | Marks | 71/112 |

FOREIGN PATENT DOCUMENTS

| | | |
|---|---|---|
| 0351195 | 1/1990 | European Pat. Off. . |
| 2339791 | 8/1973 | Fed. Rep. of Germany . |
| 2351947 | 10/1973 | Fed. Rep. of Germany . |
| 7900654 | 9/1979 | PCT Int'l Appl. . |
| 8606066 | 10/1986 | PCT Int'l Appl. . |

OTHER PUBLICATIONS

STN International, File CA, STN Accession No. No. 94(23): 186718j, Boltaev, M.: "Protection of desert fodder plants from steganosporiosis", Zashch. Kormovykh Kul't. Vred., Bolezn. Sornyakov, 1980, 91–2.

Beilsteins Handbuch der organischen Chemie, Springer-Verlag, Berlin E III/IV 24, Syst.-Nr. 3557/H3(1980).

*Primary Examiner*—Allen J. Robinson
*Attorney, Agent, or Firm*—Ernest G. Szoke; Wayne C. Jaeschke; John Daniel Wood

[57] ABSTRACT

Fungicidal solutions containing 2,4,5,6-tetrachloroisophthalodinitrile are provided. The solutions are prepared by dissolving from 5% to 12% by weight of 2,4,5,6-tetrachloroisophthalodinitrile in 1,3-dimethyl-2-imidazolidinone. The solutions are clear and can be stirred without streaking or sedimentation into water-based paints or lacquers or solvent-containing paints or lacquers.

4 Claims, No Drawings

FUNGICIDAL SOLUTION

BACKGROUND OF THE INVENTION

1. Field of the Invention

This invention relates to a fungicidal solution containing 2,4,5,6-tetrachloroisophthalodinitrile and 1,3-dimethyl-2-imidazolidinone, to a process for its production and to its use as a fungicide in paints and lacquers.

2. Discussion of Related Art

Solvent-containing and water-based paints and lacquers used for painting exposed surfaces or those which come permanently or occasionally into contact with water have to meet more stringent requirements than products which are used solely in dry environments. Apart from obvious properties, such as for example covering power, yield or ready processability, paints and lacquers used in wet environments have to meet other requirements, above all in regard to their preserving abilities. Above all, products of the type in question are expected to ensure that the coatings formed with them are protected against fungal contamination for a sufficiently long time.

2,4,5,6-Tetrachloroisophthalodinitrile (TCIPDN) has been successfully used as a fungicide which protects paints and lacquers particularly effectively against contamination by fungi, particularly molds. However, TCIPDN has the disadvantage that it is insoluble in water and insufficiently soluble in water-miscible organic solvents for industrial applications. In addition, many typical water-miscible organic solvents, such as acetone for example, involve the danger of unwanted reactions between constituents of the formulation and the solvent.

The result of this is that TCIPDN can only be added in the form of the pure substance to solvent-containing paints and lacquers, which involves packing and metering problems, whereas only aqueous fungicide dispersions can be used for water-based products. Accordingly, the fungicide has to be made up in two different formulations for one and the same application.

Accordingly, the problem addressed by the present invention was to develop a formulation for TCIPDN which would be suitable for incorporation both in solvent-containing paints and lacquers and in water-based paints and lacquers.

DESCRIPTION OF THE INVENTION

The present invention relates to a fungicidal solution containing 5 to 12% by weight 2,4,5,6-tetrachloroisophthalodinitrile and 88 to 95% by weight 1,3-dimethyl-2-imidazolidinone.

The invention is based on the observation that mixtures of TCIPDN and 1,3-dimethyl-1,2-imidazolidinone (DMI) are clear solutions within the limits mentioned which can be stirred without streaking or sedimentation not only into solvent-containing paints and lacquers, but also into water-based paints and lacquers. It has also surprisingly been found that the fungicidal solutions according to the invention are also stable at low temperatures which is an important advantage so far as their storage is concerned.

2,4,5,6-Tetrachloroisophthalodinitrile (I)

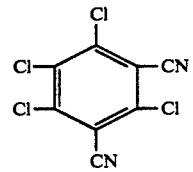

is a known compound and may be obtained by the relevant methods of preparative organic chemistry. One process for its production comprises, for example, reacting isophthalic acid dinitrile with chlorine in the presence of nitrogen [U.S. Pat. No. 3,816,515, DE-A-23 39 791, DE-A-23 51 947].

1,3-Dimethyl-2-imidazolidinone (II)

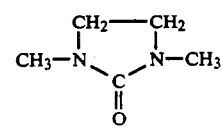

is also a known compound which may be obtained by the standard methods of preparative organic chemistry [Beilsteins Handbuch der organischen Chemie, Springer-Verlag, Berlin E III/Iv 24, Syst.-Nr. 3557/H3].

The present invention also relates to a process for the production of a fungicidal solution which is characterized in that 5 to 12% by weight 2,4,5,6-tetrachloroisophthalodinitrile is dissolved in 88 to 95% by weight 1,3-dimethyl-2-imidazolidinone. The mixture may be produced purely mechanically at room temperature, for example by stirring; no chemical reaction takes place. Fungicidal solutions containing the TCIPDN in concentrations of 10 to 12% by weight and the DMI in concentrations of 88 to 90% by weight are preferred.

The solutions according to the invention have fungicidal properties. Accordingly, the present invention also relates to the use of solutions containing 5 to 12% by weight 2,4,5,6-tetrachloroisophthalodinitrile and 88 to 95% by weight 1,3-dimethyl-2-imidazolidinone as a fungicide for protecting paints and lacquers against fungal contamination. The solutions according to the invention are also suitable for protecting products of wood, paper, textiles or leather. In addition to the substances mentioned, they may contain other typical additives, for example UV stabilizers, in concentrations of 0.1 to 0.5% by weight, based on the fungicide.

The following Examples are intended to illustrate the invention without limiting it in any way.

EXAMPLES

Example 1, Comparison Examples 1 to 5

10 g 2,4,5,6-tetrachloroisophthalodinitrile (TCIPDN) were introduced into a 100 ml round-bottomed flask and 90 g organic solvent were added at room temperature. The solution was stirred for 1 minute and immediately evaluated. The solution was then cooled to 0° C., restirred for 1 minute and immediately evaluated again. The results are summarized in Table 1.

TABLE 1

| | 10% by weight solutions of TCIPDN | | |
|---|---|---|---|
| Ex. | Organic solvent | Evaluation at 20° C. | Evaluation at 0° C. |
| 1 | 1,3-Dimethyl- | Clear solution | Clear solution |

TABLE 1-continued

| | 10% by weight solutions of TCIPDN | | |
|---|---|---|---|
| Ex. | Organic solvent | Evaluation at 20° C. | Evaluation at 0° C. |
| | 2-imidazolidone (DMI)* | | |
| C1 | N-Methyl pyrrolidone (NMP) | Cloudy solution sediment | Cloudy solution sediment |
| C2 | Dimethyl formamide (DMF) | Cloudy solution sediment | Cloudy solution sediment |
| C3 | Dimethyl sulfoxide (DMSO) | Cloudy solution sediment | Cloudy solution sediment |
| C4 | Tetrahydrofuran (THF) | Cloudy solution sediment | Cloudy solution sediment |
| C5 | Xylene | Cloudy solution sediment | Cloudy solution sediment |

*Manufacturer: Kawaken Fine Chemicals Co. Ltd., Aldrich CAS-No. 80-73-9

After prolonged standing, the solutions of Comparison Examples C1 to C5 became clear with an increase in the sediment.

We claim:

1. A fungicidal composition comprising 1,3-dimethyl-2-imidazolidinone and 2,4,5,6-tetrachloroisophthalodinitrile in a weight ratio of from 19:1 to 7.3:1.

2. A composition as claimed in claim 1 wherein said 2,4,5,6-tetrachloroisophthalodinitrile is present in an amount of from 5% to 12% by weight and said 1,3-dimethyl-2-imidazolidinone is present in an amount of from 88% to 95% by weight.

3. A composition as claimed in claim 1 wherein said weight ratio is from 9:1 to 7.3:1.

4. A composition as claimed in claim 3 wherein said 2,4,5,6-tetrachloroisophthalodinitrile is present in an amount of from 10% to 12% by weight and said 1,3-dimethyl-2-imidazolidinone is present in an amount of from 88% to 90% by weight.

* * * * *